(12) United States Patent

Kelbassa et al.

(10) Patent No.: US 9,551,134 B2
(45) Date of Patent: Jan. 24, 2017

(54) DOMESTIC-WATER SUPPLY AND WITHDRAWAL SYSTEM FOR A WASHSTAND AND SAMPLING VALVE FOR SUCH A SYSTEM

(71) Applicant: Gebr. Kemper GmbH & Co. KG Metallwerke, Olpe (DE)

(72) Inventors: Rainer Kelbassa, Attendorn (DE); Ulrich Petzolt, Friesenhagen (DE)

(73) Assignee: Gebr. Kemper GmbH & Co. KG Metallwerke, Olpe (DE)

( * ) Notice: Subject to any disclaimer, the term of this patent is extended or adjusted under 35 U.S.C. 154(b) by 228 days.

(21) Appl. No.: 14/150,555

(22) Filed: Jan. 8, 2014

(65) Prior Publication Data

US 2014/0189949 A1 Jul. 10, 2014

(30) Foreign Application Priority Data

Jan. 10, 2013 (DE) .................... 20 2013 000 217 U

(51) Int. Cl.
| | | |
|---|---|---|
| *E03C 1/01* | (2006.01) | |
| *E03C 1/02* | (2006.01) | |
| *G01N 1/20* | (2006.01) | |
| *E03B 7/08* | (2006.01) | |

(52) U.S. Cl.
CPC ............. *E03C 1/023* (2013.01); *G01N 1/2035* (2013.01); *E03B 7/08* (2013.01); *E03C 1/02* (2013.01); *G01N 2001/205* (2013.01)

(58) Field of Classification Search
CPC .............. E03C 1/023; E03C 1/02; E03B 7/08; G01N 1/2035; G01N 2001/205; C12M 33/00; C12M 37/00

USPC ............ 4/670, 676; 73/863, 863.61, 863.41; 137/861, 862, 883, 614, 877, 878, 881, 137/614.2
See application file for complete search history.

(56) References Cited

U.S. PATENT DOCUMENTS

| 1,777,453 | A | * | 10/1930 | Seery ...................... E03C 1/046 |
| | | | | 137/565.34 |
| 2,426,369 | A | | 8/1947 | Paulsen |
| 3,147,767 | A | * | 9/1964 | Goss ....................... B60S 3/044 |
| | | | | 134/17 |

(Continued)

FOREIGN PATENT DOCUMENTS

| DE | 1517879 | 3/1970 |
| DE | 3109350 | 4/1982 |

(Continued)

OTHER PUBLICATIONS

DE 102006031840—English Translation.*

*Primary Examiner* — J. Casimer Jacyna
*Assistant Examiner* — Benjamin R Shaw
(74) *Attorney, Agent, or Firm* — Richard M. Klein; Fay Sharpe LLP

(57) ABSTRACT

The present invention relates to a domestic-water supply and withdrawal system for a washstand (8) with wall-mountable angle valves (16, 18) for cold and hot water and a washstand fitting (10) which is coupled in flow communication with the associated angle valves (16, 18) via pipe or tubing sections (12, 14). The present invention wants to indicate a domestic-water supply and withdrawal system for improving the possibility of taking samples. To this end it is suggested that a sampling valve (2) is arranged between the cold-water and/or hot-water angle valve (16, 18) and the washstand fitting (10).

8 Claims, 1 Drawing Sheet

(56) References Cited

U.S. PATENT DOCUMENTS

Figure 1:
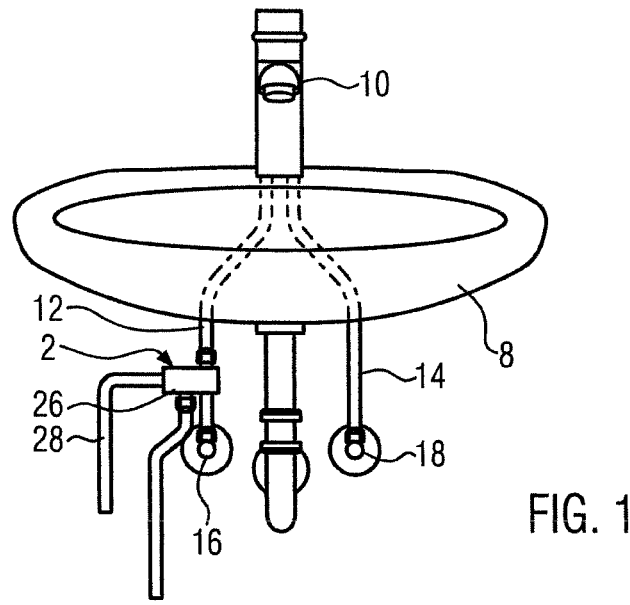

| | | | | |
|---|---|---|---|---|
| 5,293,903 A | * | 3/1994 | Appelwick | E03C 1/023 137/887 |
| 5,373,873 A | * | 12/1994 | Miller | F17C 5/06 137/883 |
| 2009/0126820 A1 | * | 5/2009 | Thomas | E03C 1/025 138/121 |

FOREIGN PATENT DOCUMENTS

| | | | | |
|---|---|---|---|---|
| DE | 4316734 | | 12/1993 | |
| DE | 19849362 | | 5/2000 | |
| DE | 10162006 | | 6/2003 | |
| DE | 69811455 | | 1/2004 | |
| DE | 202004007628 | | 10/2004 | |
| DE | 102006031840 | | 1/2008 | |
| DE | 102006031840 A1 | * | 1/2008 | ............ C12M 33/00 |
| DE | 202011001782 | | 6/2012 | |
| EP | 1 876 230 A1 | | 1/2008 | |

* cited by examiner

DOMESTIC-WATER SUPPLY AND WITHDRAWAL SYSTEM FOR A WASHSTAND AND SAMPLING VALVE FOR SUCH A SYSTEM

The present invention relates to a domestic-water supply and withdrawal system for a washstand and to a sampling valve for such a system. The present invention particularly wants to improve a sample-taking measure in an apartment or home and at a water tap, respectively.

Sometimes, such a sampling measure is carried out between an angle valve and a faucet for withdrawing water. It is the aim to take the sample as close as possible to the respective consumer. Nowadays, angle valves represent the standard connection between a concealed pipe system and a fitting positioned in a building on furniture such as washstands or washbasins of a worktop of a fitted kitchen. Corresponding washstand or kitchen sink fittings are normally configured as mixer taps. Depending on the specific structure of the washstand fitting it may happen that although in the closed state of the washstand fitting, i.e. shut-off state of the water withdrawal opening on the washstand fitting, water is prevented from running into the associated basin, the cold-water pipe leading to the fitting and the hot-water pipe leading to the fitting are short-circuited by the fitting. Known angle valves of such types normally have a connection line for connection to a mixer tap.

Sampling valves for hot-water pipe systems are generally known. According to the German Drinking Water Ordinance such sampling valves are normally connected in a hot-water pipe system directly to an outlet of a hot-water boiler in flow direction behind said boiler. Thus, sampling as well as analyzing of the hot water as to microbial contamination can be carried out directly behind the hot-water boiler.

Moreover, according to the German Drinking Water Ordinance a sample has to be taken in the hot-water piping at the most distant place. To this end the sample is normally taken there on a consumer, particularly a faucet. To this end the faucet is operated, i.e. opened, and the hot water discharged thereby is obtained as a sample under well-defined boundary conditions and analyzed as to microbial contamination.

To rule out microbial ingress from the outside into the system during analysis, a filter sieve is normally dismantled in the case of such a withdrawal from a faucet before a water sample is taken. When water is withdrawn directly at the mixing fitting or the faucet, the mixing of hot and cold water can often not be avoided.

In the case of sampling valves to be connected directly behind a boiler, one usually starts from a unit, i.e. a separate uniform element which is inserted into the outlet line of the hot-water boiler under separation of a pipe section.

The present invention is based on the problem to indicate a domestic-water supply and withdrawal system of the aforementioned type for improving the possibility of taking samples.

To achieve this object, the present invention suggests the arrangement of a sampling valve between the cold-water angle valve and the washstand fitting. As a supplement or alternative, a sampling valve may be provided between the angle valve for the hot water and the washstand fitting. This makes it possible to take a sample near the consumer.

According to a preferred development of the present invention a backflow preventer is provided between the sampling valve and the washstand fitting. This prevents a situation where the hot-water pipe is short-circuited with the cold-water pipe via the washstand fitting and that thus, while a sample is being taken from the cold-water pipe, hot water is also withdrawn in reality, which leads to distorted results and therefore to wrong conclusions because of the samples taken.

Preferably, the backflow preventer is arranged in a housing of the sampling valve, normally captively mounted there, preferably by way of a retaining ring embedded in a groove recessed on the housing. Captively means here in particular that the backflow preventer cannot be dismantled by taking simple mechanical measures. The further development ensures that the sampling valve is always installed together with the backflow preventer in a reliable manner. The mechanic installing the supply and withdrawal system for the washstand cannot easily remove the backflow preventer from the housing and thus mount the sampling valve without backflow preventer.

Insofar as this protective right application regards a "washstand", this may be a washstand for body care or for cleaning equipment or foodstuff. The present invention is not specifically limited to a supply and withdrawal system for domestic water that is solely mounted in a bathroom. The present invention particularly aims at those supply and withdrawal systems where due to the specific design of the washstand fitting it may happen that the cold-water supply and the warm-water supply are short-circuited via the washstand fitting. The pipe sections of the subject matter of the utility model are normally typically provided on a washstand fitting and serve the connection of the fitting directly to the angle valve. Alternatively, flexible tubing sections may also be provided. Instead of this angle valve, in the supply and withdrawal system according to the invention, the sampling valve for taking samples is provided, at which the pipe sections are connected.

The sampling valve of the present invention which as such is protected with claim 6 comprises a one-part or multi-part housing forming an inlet, outlet and sampling opening. The inlet opening and the outlet opening are interconnected via a flow passage formed in the housing, i.e. they are communicating with one another. Furthermore, a valve body is movably arranged in the housing. This valve body is enclosed by the housing. The valve body cooperates with a valve seat at the housing side. In a closing position the valve body closes the sampling opening relative to the flow passage. In an open position, the valve body permits a flow from the flow passage to the sampling opening. Moreover, in the sampling valve according to the invention a backflow preventer is assigned to the outlet opening.

According to the preferred developments according to claims 7 and 8 the backflow preventer is arranged in the previously discussed manner on the housing of the sampling valve and connected thereto, respectively, especially captively and via a retaining ring.

Figure 2:
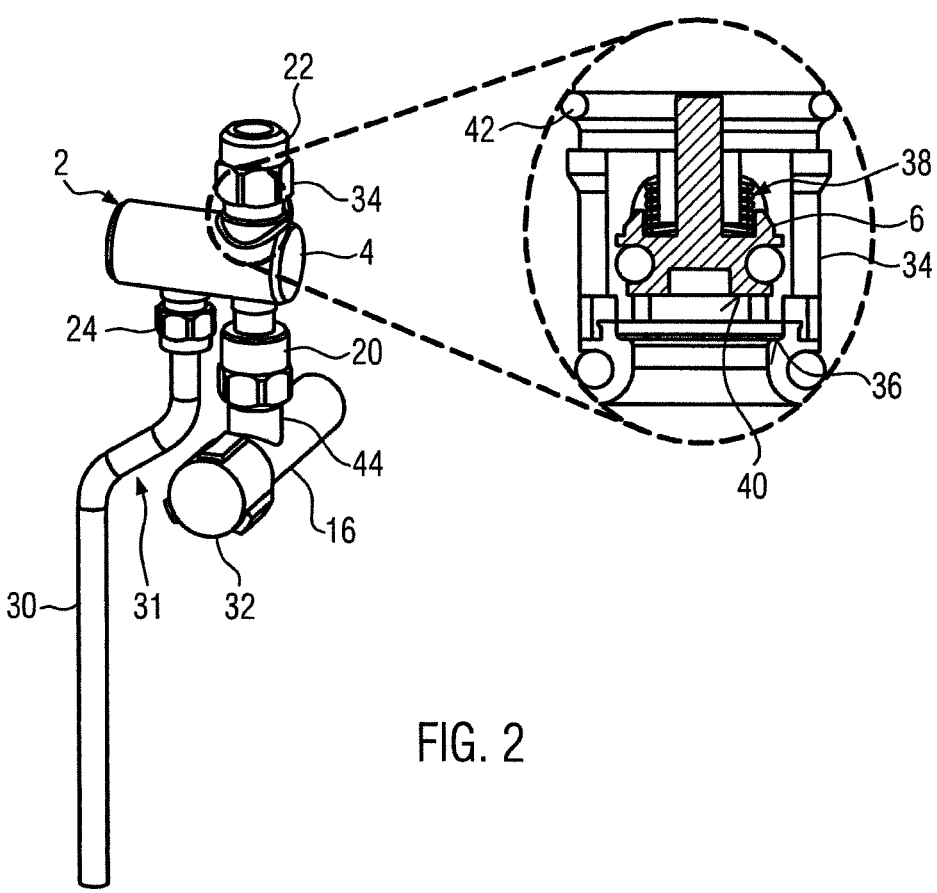

Further details and advantages of the present invention become apparent from the following description of an embodiment in combination with the drawing, in which FIG. 1 shows a domestic-water supply and withdrawal system; and FIG. 2 is an enlarged view of a sampling valve of the domestic-water supply and withdrawal system shown in FIG. 1, with a backflow preventer received in the housing thereof.

The domestic-water supply and withdrawal system shown in FIG. 1 comprises a washstand 8 and a washstand fitting 10 secured thereto in the form of a faucet. A hot-water pipe 12 and a cold-water pipe 14 lead to the faucet 10. The faucet 10 is configured as a mixer tap so that upon operation of said faucet, the water supplied by means of the hot-water pipe 12 and the cold-water pipe 14 can be mixed to a predetermined temperature and discharged therefrom.

The hot-water pipe 12 and the cold-water pipe 14, respectively, are connected via a hot-water side angle valve 16 and a cold-water side angle valve 18, respectively, to a hot-water and a cold-water conducting piping of a building. Between the hot-water side angle valve 16 and the faucet 10 the sampling valve 2 is connected underneath the washstand 8 directly in the flow direction of the hot water behind the hot-water side angle valve 16 to said valve.

An enlarged view of the sampling valve 2 and of the hot-water side angle valve 16 connected thereto is shown in FIG. 2. The sampling valve 2 comprises an inlet connection piece 20, an outlet connection piece 22 and a withdrawal connection piece 24. The inlet connection piece 20 is configured such that it is made to fit angle valves with an outgoing connection line 44 of e.g. 10 mm. The withdrawal connection piece 24 has e.g. a ⅜" connection thread with a threaded connection with compression fitting.

The sampling valve housing 4 is T-shaped, the roof of the T-shape being formed by the inlet and outlet connection pieces 20, 22 which are in flow passage communication with each other. In a base of the housing 4 vertically extending to the roof of the T-shape, a valve element is installed that releases or closes the withdrawal connection piece 24, which is vertically outgoing from the base in parallel with the inlet connection piece 20, for a flow connection to a flow between the inlet and the outlet connection pieces 20, 22. The valve element can be operated via an inner multisided receptacle 26 by an inner hexagon wrench 28. In the closed state of the valve, water can unimpededly flow in the main flow direction of the sampling valve 2 (between the inlet connection piece 20 and outlet connection piece 22). In the opened state of the valve, water is discharged via the withdrawal connection piece 24. Hence, a sample can be taken without operating the faucet 10.

To ensure the taking of samples in compliance with the standards, as shown in FIG. 2, a withdrawal pipe section 30 is screwed onto the withdrawal connection piece 24 and has an offset 31. This offset 31 is dimensioned such that the withdrawal pipe piece 30 does not intersect a closing valve 32 of the hot-water side angle valve 16.

Apart from the valve insert, the housing 4 comprises a non-return valve 6, which is shown in FIG. 2 at the right side on an enlarged scale, within a pipe section 34 leading to the outlet connection piece 22. The non-return valve 6 comprises a tension or compression spring 38 in vertical direction, said spring pressing a sealing surface 40 against a corresponding abutment surface 36 provided at the top side inside the housing 4.

When hot water does not flow from the hot-water side angle valve 16 through the hot-water pipe 12 in the opened state of the faucet 10, a return flow of the water from the faucet 10 to the withdrawal connection piece 24 is shut off by the sealing abutment of the sealing surface 40 against the abutment surface, which abutment is enforced by the tension spring 38. The non-return valve 6 is captively held by means of a retaining ring 42 inside the housing 4. Hence, the housing 4 forms the sampling valve 2 with the valve element contained in said housing and with the non-return valve 6.

LIST OF REFERENCE NUMERALS 2 sampling valve
4 housing
6 backflow preventer/non-return valve
8 washstand
10 washstand fitting, faucet
12 hot-water pipe
14 cold-water pipe
16 hot-water side angle valve
18 cold-water side angle valve
20 inlet connection piece
22 outlet connection piece
24 withdrawal connection piece
26 inner multisided receptacle
28 inner hexagon wrench
30 withdrawal pipe section
31 offset
32 closing cock
34 pipe section
36 abutment surface
38 tension spring/compression spring
40 sealing surface
42 retaining ring
44 connection pipe

The invention claimed is:

1. A domestic-water supply and withdrawal system for a washstand with wall-mountable angle valves (16, 18) for cold and hot water and a washstand fitting (10) which is coupled in flow communication with the associated angle valves (16, 18) via pipe or tubing sections (12, 14),
    wherein a sampling valve (2) is arranged between the cold-water and/or hot-water angle valve (16, 18) and the washstand fitting (10);
    wherein a backflow preventer (6) is arranged between the sampling valve (2) and the washstand fitting (10); and
    wherein the backflow preventer (6) is secured via a retaining ring (42) to a housing (4) of the sampling valve (2).

2. The domestic-water supply and withdrawal system according to claim 1, characterized in that the backflow preventer (6) is arranged in the housing (4) of the sampling valve (2).

3. The domestic-water supply and withdrawal system according to claim 1, characterized in that the backflow preventer (6) is captively received in the housing (4) of the sampling valve (2).

4. A domestic-water supply and withdrawal system for a washstand with wall-mountable angle valves (16, 18) for cold and hot water and a washstand fitting (10) which is coupled in flow communication with the associated angle valves (16, 18) via pipe or tubing sections (12, 14), characterized in that a sampling valve (2) is arranged between the cold-water and/or hot-water angle valve (16, 18) and the washstand fitting (10); wherein the sampling valve has a housing (2) having an inlet opening (20), an outlet opening (22) and a sampling opening (24); wherein the inlet opening (20) and the outlet opening (22) are in communication with each other via a flow passage formed in the housing (2); and wherein a backflow preventer (6) is arranged between the sampling valve (2) and the washstand fitting (10); and wherein the backflow preventer (6) is secured via a retaining ring (42) to the housing (4) of the sampling valve (2).

5. A sampling valve (2) for a domestic-water supply and withdrawal system comprising a housing (4) having an inlet (20), outlet (22) and sampling opening (24), wherein the inlet opening (20) and the outlet opening (22) are in communication with each other via a flow passage formed in the housing (4), and wherein the housing (4) encloses a valve body movably arranged therein, which in its closing position shuts off the sampling opening (24) from the flow passage and which in an open position opens the flow passage to the sampling opening (24), characterized in that a backflow preventer (6) is arranged within the flow passage and assigned to the outlet opening (22), and the backflow preventer (6) is secured via a retaining ring (42) to the housing (4) of the sampling valve (2).

6. The domestic-water supply and withdrawal system according to claim 2, characterized in that the backflow preventer (6) is captively received in the housing (4) of the sampling valve (2).

7. The domestic-water supply and withdrawal system according to claim 4, characterized in that the backflow preventer (6) is captively received in the housing (4) of the sampling valve (2).

8. A sampling valve (2) for a domestic-water supply and withdrawal system comprising a housing (4) having an inlet (20), outlet (22) and sampling opening (24), wherein the inlet opening (20) and the outlet opening (22) are in communication with each other via a flow passage formed in the housing (4), and wherein the housing (4) encloses a valve body movably arranged therein, which in its closing position shuts off the sampling opening (24) from the flow passage and which in an open position opens the flow passage to the sampling opening (24), characterized in that a backflow preventer (6) is arranged within the flow passage and assigned to the outlet opening (22), the backflow preventer (6) is arranged in the housing (4) of the sampling valve (2), and the backflow preventer (6) is secured via a retaining ring (42) to the housing (4) of the sampling valve (2).

\* \* \* \* \*